United States Patent [19]
Whitehead

[11] Patent Number: 5,342,576
[45] Date of Patent: Aug. 30, 1994

[54] MAGNESIUM MANGANESE ALLOY

[75] Inventor: Derek J. Whitehead, Poynton, Great Britain

[73] Assignee: Castex Products Limited, Stockport, Great Britain

[21] Appl. No.: 782,810

[22] Filed: Oct. 25, 1991

[30] Foreign Application Priority Data

Oct. 25, 1990 [GB] United Kingdom ............... 9023270

[51] Int. Cl.$^5$ .............................................. C22C 23/00
[52] U.S. Cl. ...................................... 420/413; 148/420; 420/409; 420/412; 420/414; 603/93; 603/890.1
[58] Field of Search ............... 420/409, 412, 413, 414; 148/406, 420; 604/890.1, 93

[56] References Cited

U.S. PATENT DOCUMENTS

| | | | |
|---|---|---|---|
| 3,182,390 | 5/1965 | Foerster | 420/409 |
| 4,863,455 | 9/1989 | Whitehead | 604/890.1 |

FOREIGN PATENT DOCUMENTS

| | | |
|---|---|---|
| 470538 | 11/1974 | Australia . |
| 6466280 | 3/1981 | Australia . |
| 393837 | 6/1933 | United Kingdom . |
| 1102979 | 2/1968 | United Kingdom . |

OTHER PUBLICATIONS

Stuedeman et al, American Journal Veterinary Research, vol. 45, No. 4 (Apr. 1984), Efficacy of a Large Magnesium Alloy Rumen Bolus in the Prevention of Hypomagnesemic Tetany in Cows, pp. 698–702.

*Primary Examiner*—Richard Dean
*Assistant Examiner*—Robert R. Koehler
*Attorney, Agent, or Firm*—Dennison, Meserole, Pollack & Scheiner

[57] ABSTRACT

The invention provides a magnesium manganese alloy suitable for use in the production of a pellet 10 for administration to a ruminant by dposition in its rumenoreticular sac. A typical pellet 10 comprises a magnesium alloy tube 12 enclosing a degradable core formed of plurality of tablets 14, 16. The magnesium alloy used in the construction comprises at least 90% by weight of magnesium, uyp to 1% zinc and up to 2% of manganese. Preferably the alloy may further include aluminium, silicon or zirconium along with iron and beryllium. When deposited in an animal's rumen the alloy reacts with the rumen juices to form an anodic film over the exposed surface of the tube 12. This prevents corrosion or dissolution of the tube 12 except at its exposed ends where galvanic corrosion by coupling with the electrically conductive core 14, 16 is provided. The normal requirement of a non-degradable exterior coating e.g. resin for the tube exterior is obviated.

5 Claims, 1 Drawing Sheet

MAGNESIUM MANGANESE ALLOY

BACKGROUND OF THE INVENTION

This invention concerns alloy of which constituents include primarily magnesium and manganese, which alloy are particularly suitable for production of or incorporation into products in the form of pellets for administering to ruminants by deposition into the rumeno-reticular sacs.

Pellets containing magnesium and other metallic animal dietary supplements or active agents can be administered, for example by means of an oesophageal balling gun, to ruminants such that they are dissolved in the rumen juices. Such dissolution or corrosive degradation takes place over a period of several weeks so as to provide a continuous or alternatively a dosed supply of magnesium with or without other valuable metallic elements and/or active agents for assimilation by a ruminant.

In order that the amount of magnesium or active agent assimilated by the ruminant can be accurately determined and controlled it is essential that the corrosion or dissolution of the pellet can be accurately determined. It is possible to control corrosion of magnesium alloy in rumen juices by adding aluminium, copper or zinc in predetermined quantities. Such additional elements may also assist or control castability and the mechanical properties of the alloy and of a pellet cast therefrom.

A common form of pellet for administration to a ruminant comprises a hollow tubular body of a magnesium based alloy, its internal cavity containing, usuaully a plurality of tablets or a preformed body containing a biologically active agent such as an anthelmintic or a similar active drug.

In the rumen juices of a ruminant corrosion or dissolution of such an exterior magnesium alloy tube causes release of the active agent contained in its cavity.

It will be appreciated that, for such constructions, it is possible for corrosion of the magnesium alloy tube to proceed not only from an exposed end but also from its peripheral surface. Such corrosion can lead to a weakening of the overall structure or a possibility of release of biological agents within the cavity of the tube earlier than intended. In order to prevent this the exterior surface of the magnesium tube can be provided with an external protective coating. This coating should resist corrosion by rumen juices and may be, for example of synthetic plastic material. In a known embodiment there is provided a plurality of plastic rings or tyres each extending around the exterior surface of the magnesium tube. In this way as the magnesium tube degrades from an exposed end successive rings or tyres drop away to allow access for the rumen juices to the tube and the tablet enclosed therein.

One known way of controlling corrosion of a magnesium alloy component is described in European Patent Application No. 0 284 258. In this application a magnesium alloy tube is galvanically coupled to an electrically conductive component containing material lower in the electrochemical series than magnesium. For example, an electrically conductive material may be dispersed throughout the body or tablets containing the biologically active material. In this way galvanic corrosion of the magnesium alloy proceeds at a predetermined and measurable rate so that the pellet may be constructed to dispense a biologically active material at predetermined intervals.

However, in order to prevent galvanic corrosion from corroding or otherwise weakening the exterior surface of a tube it is again necessary to provide either an epoxy resin coating or a plurality of non-degradable plastic rings around the exterior of the tube. Such additional components complicate and increase the cost of the manufacturing process of the pellet and limit the configurations which can be used. However, if the contents of the interior of a tubular bolus are to be dispensed at the require predetermined intervals the exterior surface of the tubular component must be protected against corrosion.

It would be an advantage to provide a pellet having a tubular magnesium alloy component in which the corrosion rate of the exterior surface is controllable without resort to an additional protective sleeve or coating.

SUMMARY OF THE INVENTION

According to this invention there is provided a magnesium alloy suitable for use in the production of a pellet for administration to a ruminant by deposition into its rumenoreticular sac characterised in that the alloy comprises at least 90% by weight of magnesium, up to 1% zinc and up to 2% manganese.

Additionally the alloy may contain other elements and in a first preferred composition additionally comprises aluminium up to 1%, silicon up to 1%, iron up to 0.03%, and beryllium up to 0.002%.

An alternative composition of the alloy additionally includes zirconium up to 0.5% zinc up to 1% and iron up to 0.03%. In this aspect of the invention manganese preferably comprises approximately 0.4% of the alloy and neither silicon or aluminium are included.

It has been found that when a magnesium alloy containing manganese according to the preferred compositions is placed in the rumeno reticular sac of an animal, an anodic film is developed where the magnesium alloy contacts the rumen juices. This anodic film which may contain alkali metal phosphates effectively protects the magnesium alloy from corrosion or dissolution into the rumen juices. By providing a pellet formed as a tubular magnesium element enclosing an electrically conductive degradable core which is galvanically coupled to the magnesium alloy tube, galvanic corrosion will proceed at the exposed ends of the magnesium alloy tube only thus causing the axial length of the tube to reduce with time spent in the rumen liquor.

BRIEF DESCRIPTION OF THE DRAWINGS

The invention will be described further by way of example with reference to the accompanying drawings in which.

DESCRIPTION OF THE PREFERRED EMBODIMENTS

Figure 1:
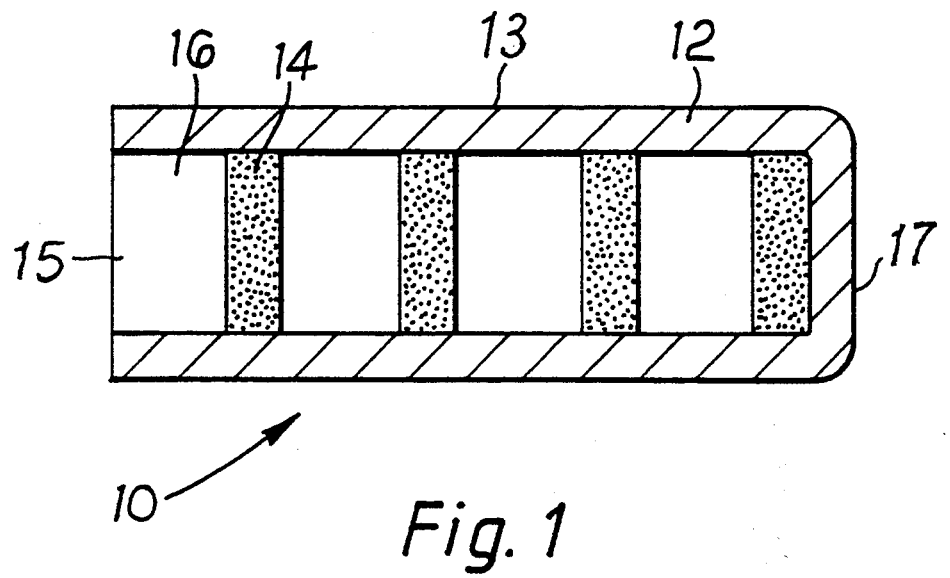
FIG. 1 is a sectional side view of a first preferred embodiment of the invention.

Referring firstly to FIG. 1 of the drawings, a first embodiment of the invention formed as a bolus or pellet is indicated generally by the reference numeral 10. The pellet 10 is formed generally from a tubular outer sheath or body 12 of a magnesium alloy which has a lateral external surface 13 between ends 15 and 17, end 15 being open and end 17 being closed. A typical magnesium alloy comprises manganese up to 2% by weight, and up to 1% each of aluminium, zinc and silicon, up to 0.03% iron and up to 0.002% beryllium, the remainder being magnesium and trace elements. It will be understood that the percentages of aluminium and iron can be varied or modified to control the corrosion rate of the alloy in rumen juices. In this way the pellet can be constructed to erode at a predetermined and predictable rate thereby giving a known lifespan within an animal's rumen.

The alloy body itself is formed using conventional melting techniques and may be produced by casting process, for example, gravity or pressure die casting.

The tubular body 12 defines within it a cavity which is filled with a plurality of pre-formed tablets 14, 16. The method of construction of these tablets and the materials comprising them depends on the physical properties of the biologically active material to be contained therein and on the frequency with which it is intended to provide such material to the animal in question. The illustrated embodiment is a pulsed dose bolus intended to release pulses of a biologically active material, for example, benzimidazol or a similar active material at predetermined intervals.

Thus, active tablets 14 are formed from a mixture comprising 77% by weight of finely divided iron, 10% by weight of benzimidazol, 7.5% by weight of sucrose and 5.5% by weight of graphite. The sucrose and benzimadazol together form binding agents between the remaining components of the material and dispersal of graphite throughout the tablet provides the required electrical conductivity for galvanic corrosion and coupling with the magnesium alloy tube 12. The finely divided iron provides a weighting agent such that the density of the bolus 10 as a whole is sufficient to cause its retention within the stomach of an animal.

The magnesium alloy tube 12 corrodes in an animal's rumen juices at a specific constant rate and therefore to provide pulsed doses of benzimidazol the active tablets 14 are interspersed in the tubular element 12 by packing tablets 16. The axial length of these tablets and their respective rate of degradation in the rumen juices determines the time interval between the rumen juices contacting successive active tablets and hence the time between successive pulsed releases of benzimidazol to the rumen.

It should be noted that benzimidazol is not the only biologically active material which can be included in the active tablet 14 and other materials are also usable. Examples of such materials are growth improving agents, anthelmintics, bacteriocidal, fungicidal or other veterinary pharmaceutical compounds. Trace elements which are required in the diet of the animal may also be included as may vitamins and other similar materials. In this way it should be noticed that the tablets are not usually formed at elevated temperatures which would adversely affect most pharmaceutical compounds.

In the illustrated embodiment the packing tablets 16 are formed from 75% by weight finely divided iron shot or powder 15% sulphur, 6% graphite, 2.5% sucrose and 1.5% zinc stearate. The graphite provides the packing tablet 16 with the electrical conductivity required to cause galvanic coupling with the magnesium alloy tube and hence galvanic corrosion thereof. The iron shot or iron powder is provided as a weighting element as for the active tablet 14.

In an alternative embodiment or where the drug or active agent is fairly potent the tablet 14 may be included as an insert in the packing tablet 16. Thus, the packing tablets will be formed having a depression or space at one axial end thereof to locate therein the benzimidazol containing tablet 14.

The insertion of a bolus including a tube formed from a magnesium alloy as disclosed for example in European Patent No. 0 240 109 into the rumen of an animal will normally subject it to degradation over its exposed exterior surface when attacked by the rumen juices. Thus, in order to prevent breaking up of the bolus over a short period of time it is usually necessary to provide a non-degradable exterior coating. Such coatings may be of a resin or of a succession of plastic rings which may be shed along with degradation of the supporting magnesium alloy tube wall.

With a bolus according to the present invention however once the bolus is inserted into the rumen of an animal the magnesium alloy reacts with the rumen juices to develop an anodic film on its exterior surface. This anodic film which may include alkali metal phosphates prevents the rumen juices from attacking the magnesium alloy and thus causing its corrosion or dissolution. The exposed ends of the magnesium alloy tube are degraded by way of galvanic corrosion through coupling with the electrically conductive material placed in the core. This continuous galvanic degradation prevents the formation of an anodic film at this point i.e. the exposed ends and thus provides dosing of magnesium to the animal and the exposure of successive tablets or portions of the core to attack by the rumen juices.

Figure 2:
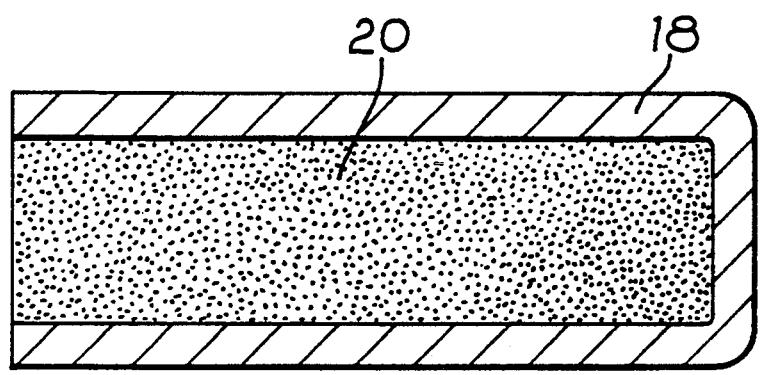
FIG. 2 is a similar view of a second embodiment of the invention.

Turning now to FIG. 2, a second embodiment of the invention provides for a continuous release of an active agent by providing a tubular element 18 of a magnesium alloy generally as indicated in the first embodiment and a solid core 20 formed of a pasty material inserted therein. This core 20 is degradable in the rumen liquor and contains evenly dispersed therethrough a biologically active material, for example, benzimidazol, an electrically conductive material, for example, graphite, and a weighting material, for example, finely divided iron shot. Thus, the core 20 as a whole fulfills the requirements of increasing the density of the bolus sufficiently so that it will be retained within the rumen of the animal and provides galvanic coupling to ensure the galvanic corrosion of the magnesium alloy tube element surrounding it.

In this embodiment it will be understood that the core 20 degrades at a constant rate under action of the rumen juices and in relation to the galvanic corrosion of the magnesium alloy tube 18. Thus, the biologically active material contained in the core 20 is supplied to the rumen at a constant rate over the lifetime of the bolus. The iron weighting material ensures that the density of the bolus during its active life span is sufficient to ensure its retention in the rumen of the animal. When the average density of the bolus drops below 2.25 gm/ml the bolus may be expelled from the rumen of the animal.

Each of the above described embodiments may also be formed using a modified magnesium alloy in which the percentage by weight of manganese is reduced to 0.4 or 0.5% and the alloy further includes zirconium at 0.5% by weight and 1% by weight of zinc.

In this embodiment no silicon or aluminium is Permitted since these elements are incompatible with zirconium.

What is claimed is:

1. A pellet for administration to a ruminant by deposition into a rumeno-reticular sac, comprising a core comprising a biologically active material and an outer sheath having a lateral external surface between two ends, and formed of a magnesium alloy consisting essentially of, by weight:
   at least 90% magnesium;
   up to 1% zinc;
   about 0.4 to 2% manganese;
   up to 1% aluminum;
   up to 1% silicon;
   up to 0.03% iron;
   up to 0.002% beryllium; and
   up to 0.5% zirconium,
   said lateral external surface being resistant to corrosion by rumen juices by means of an anodic film which forms on the surface upon exposure to rumen juices.

2. A pellet according to claim 1, wherein said alloy comprises, by weight, about zinc.

3. A pellet according to claim 1, wherein silicon and aluminum are not present.

4. A pellet according to claim 1 or 2, wherein said core is an electrically conductive degradable core galvanically coupled to said sheath.

5. A pellet according to claim 1, wherein said outer sheath is uncoated.

* * * * *